US012678128B2

(12) United States Patent
Isla Garcia et al.

(10) Patent No.: US 12,678,128 B2
(45) Date of Patent: Jul. 14, 2026

(54) SYSTEM AND METHOD FOR NON-INVASIVELY SENSING A BLOOD VESSEL

(71) Applicant: Becton, Dickinson and Company, Franklin Lakes, NJ (US)

(72) Inventors: Julio Agustin Isla Garcia, Irvine, CA (US); Xiaolong Li, Irvine, CA (US); Rendle Lamarr Myles, Jr., Covina, CA (US); Alexander H. Siemons, Yorba Linda, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 403 days.

(21) Appl. No.: 18/157,297

(22) Filed: Jan. 20, 2023

(65) Prior Publication Data

US 2023/0148992 A1     May 18, 2023

Related U.S. Application Data

(63) Continuation of application No. PCT/US2021/041660, filed on Jul. 14, 2021.

(60) Provisional application No. 63/054,558, filed on Jul. 21, 2020.

(51) Int. Cl.
*A61B 8/00*          (2006.01)
*A61B 8/08*          (2006.01)

(52) U.S. Cl.
CPC .......... *A61B 8/0891* (2013.01); *A61B 8/4477* (2013.01)

(58) Field of Classification Search
CPC ... A61B 8/0891; A61B 8/4477; A61B 8/4236; A61B 8/5223
See application file for complete search history.

(56) References Cited

U.S. PATENT DOCUMENTS

| | | | | |
|---|---|---|---|---|
| 2011/0319767 | A1* | 12/2011 | Tsuruno | A61B 8/4227 600/459 |
| 2015/0216425 | A1* | 8/2015 | Gladshtein | A61B 5/02416 600/407 |
| 2017/0143309 | A1* | 5/2017 | Seki | G16H 50/30 |
| 2019/0380677 | A1* | 12/2019 | Ono | A61B 8/4236 |

* cited by examiner

*Primary Examiner* — Michael J Carey
*Assistant Examiner* — Zainab Mohammed Aldarraji
(74) *Attorney, Agent, or Firm* — Getz Balich LLC

(57) ABSTRACT

A system and method for non-invasively sensing a blood vessel are provided. The system includes a sensor and a controller. The sensor has an array of ultrasound transducers that includes at least a first ultrasound transducer and a second ultrasound transducer. The controller is in communication with the first ultrasound transducer and the second ultrasound transducer, and a memory storing instructions. The instructions when executed cause the controller to: a) control the first ultrasound transducer to produce a first ultrasonic beam, to receive reflected first ultrasonic signals, and to communicate first sensed signals to the controller; b) control the second ultrasound transducer to produce a second ultrasonic beam, to receive reflected second ultrasonic signals, and to communicate second sensed signals to the controller; c) determine a first vessel diameter value; d) determine a second vessel diameter value; and e) determine a pulse wave velocity value.

21 Claims, 5 Drawing Sheets

SYSTEM AND METHOD FOR NON-INVASIVELY SENSING A BLOOD VESSEL

This application claims the benefit of PCT/US2021/041660, filed Jul. 14, 2021, which claims the benefit of U.S. Patent Application Ser. No. 63/054,558, filed Jul. 21, 2020, the entireties of each of which are hereby incorporated herein by reference.

BACKGROUND OF THE INVENTION

1. Technical Field

The present disclosure relates to systems and methods for non-invasively sensing blood vessels in general, and to systems and methods for non-invasively determining physiologic parameters including and based on arterial diameter and local pulse wave velocity values in particular.

2. Background Information

Healthcare providers often monitor one or more physiologic parameters of a patient during diagnosis and treatment. A wide variety of monitoring devices have been developed to meet this need and have become an indispensable part of modem medicine. For example, arterial blood pressure is a key parameter that historically has been determined using a sphygmomanometer (i.e., a blood pressure cuff). The sphygmomanometer is typically operated to apply sufficient force to initially occlude the flow of blood through the brachial artery within an upper arm. The force is released to determine the systolic and diastolic blood pressure. This process may be described as being at least partially invasive in view of the application of the external force. Arterial tone is another key physiologic parameter. Some existing methodologies for estimating an arterial tone value measure the arrival of a pulse wave relative to an electrocardiogram signal (i.e., "ECG" or EKG"). Such methods of estimating arterial tone are susceptible to changes in heart contractility and central arterial tone, which can introduce errors into the estimation. Local arterial tone estimates are useful for assessing the performance of vasoactive agents, and possible for determining the state of sepsis within a subject. In fact, prior art methods of which we are aware cannot distinguish between central and local arterial tone. What is needed is a system and method that provides information in a non-invasive manner that can be used to infer physiologic parameters with greater specificity and sensitivity.

SUMMARY

According to an aspect of the present disclosure, a system for non-invasively sensing a blood vessel is provided that includes a sensor and a controller. The sensor has an array of ultrasound transducers that includes at least a first ultrasound transducer and a second ultrasound transducer. The array has a first column, a first row, and a second row, and the first row is spaced apart from the second row by an intercolumn distance. The first ultrasound transducer is disposed in the first column and the first row, and the second ultrasound transducer is disposed in the first column and the second row. The controller is in communication with the first ultrasound transducer and the second ultrasound transducer, and a memory storing instructions. The instructions when executed by the controller cause the controller to: a) control the first ultrasound transducer to produce a first beam of first ultrasonic signals and to receive reflected first ultrasonic signals, and to communicate first sensed signals to the controller that are representative of the reflected first ultrasonic signals; b) control the second ultrasound transducer to produce a second beam of second ultrasonic signals and to receive reflected second ultrasonic signals, and to communicate second sensed signals to the controller that are representative of the reflected second ultrasonic signals; c) determine a first vessel diameter value using the first sensed signals; d) determine a second vessel diameter value using the second sensed signals; and e) determine a pulse wave velocity value using the first sensed signals and the second sensed signals.

In any of the aspects or embodiments described above and herein, the first beam of first ultrasonic signals may be configured to have a first focal zone disposed at a predetermined depth, and a first width at the predetermined depth that is equal to or greater than a predetermined vessel diameter.

In any of the aspects or embodiments described above and herein, the second beam of second ultrasonic signals may be configured to have a second focal zone disposed at the predetermined depth, and a second width at the predetermined depth that is equal to or greater than the predetermined vessel diameter.

In any of the aspects or embodiments described above and herein, the instructions when executed may cause the controller to determine a first position of an anterior wall portion of the blood vessel using the first sensed signals, and determine a first position of a posterior wall portion of the blood vessel using the first sensed signals, and determine the first vessel diameter value using the determined first position of the anterior wall portion of the vessel and the determined first position of the posterior wall portion.

In any of the aspects or embodiments described above and herein, the instructions when executed may cause the controller to determine a second position of the anterior wall portion of the blood vessel using the second sensed signals, and determine a second position of the posterior wall portion of the blood vessel using the second sensed signals, and determine the second vessel diameter value using the determined second position of the anterior wall portion of the vessel and the determined second position of the posterior wall portion.

In any of the aspects or embodiments described above and herein, the instructions when executed may cause the controller to identify a pulse wave traveling past a first vessel axial position using the determined first position of the anterior wall portion of the blood vessel and the determined first position of the posterior wall portion, and to identify the pulse wave traveling past a second vessel axial position using the determined second position of the anterior wall portion of the blood vessel and the determined second position of the posterior wall portion, and to determine a period of elapsed time between the pulse wave passing the first vessel axial position and the pulse wave passing the second vessel axial position.

In any of the aspects or embodiments described above and herein, the first vessel axial position and the second vessel axial position may be separated by the intercolumn distance.

In any of the aspects or embodiments described above and herein, the instructions when executed may cause the controller to identify a pulse wave traveling past a first vessel axial position using the first sensed signals and to identify the pulse wave traveling past a second vessel axial position using the second sensed signals, and to determine a period of elapsed time between the pulse wave passing the first vessel axial position and the pulse wave passing the second vessel axial position.

In any of the aspects or embodiments described above and herein, the first column may be orthogonal to the first row and to the second row.

In any of the aspects or embodiments described above and herein, the array of ultrasound transducers may have "N" number of columns, where "N" is an integer greater than one, and may have "M" number of rows, where "M" is an integer equal to or greater than two.

According to an aspect of the present disclosure, a method of non-invasively sensing a blood vessel is provided. The method includes: a) providing a sensor having an array of ultrasound transducers that includes at least a first ultrasound transducer and a second ultrasound transducer, the array having a first column, a first row, and a second row, the first row spaced apart from the second row by an intercolumn distance, the first ultrasound transducer disposed in the first column and the first row, and the second ultrasound transducer disposed in the first column and the second row, and a controller in communication with the first ultrasound transducer and the second ultrasound transducer; b) disposing the sensor on a skin surface of a subject so that the first column substantially aligns with an axial length of the blood vessel; c) operating the first ultrasound transducer to interrogate the blood vessel with a first beam of first ultrasonic signals, and to receive reflected first ultrasonic signals, the first ultrasound transducer configured to produce first sensed signals representative of the reflected first ultrasonic signals; d) operating the second ultrasound transducer to interrogate the blood vessel with a second beam of second ultrasonic signals, and to receive reflected second ultrasonic signals, the second ultrasound transducer configured to produce second sensed signals representative of the reflected second ultrasonic signals; e) determining a first vessel diameter value using the first sensed signals; f) determining a second vessel diameter value using the second sensed signals; and g) determining a pulse wave velocity value using the first sensed signals and the second sensed signals.

In any of the aspects or embodiments described above and herein, the blood vessel may be an artery.

In any of the aspects or embodiments described above and herein, the first beam of first ultrasonic signals may be configured to have a first focal zone disposed at a predetermined depth, and a first width at the predetermined depth that is equal to or greater than a predetermined vessel diameter.

In any of the aspects or embodiments described above and herein, the step of determining said first vessel diameter value using the first sensed signals may include determining a first position of an anterior wall portion of the blood vessel using the first sensed signals, and determining a first position of a posterior wall portion of the blood vessel using the first sensed signals, and determining the first vessel diameter value using the determined first position of the anterior wall portion of the vessel and the determined first position of the posterior wall portion.

In any of the aspects or embodiments described above and herein, the step of determining said second vessel diameter value using the second sensed signals may include determining a second position of the anterior wall portion of the blood vessel using the second sensed signals, and determine a second position of the posterior wall portion of the blood vessel using the second sensed signals, and determine the second vessel diameter value using the determined second position of the anterior wall portion of the vessel and the determined second position of the posterior wall portion.

In any of the aspects or embodiments described above and herein, the step of determining said pulse wave velocity value using the first sensed signals and the second sensed signals may include identifying a pulse wave traveling past a first vessel axial position using the determined first position of the anterior wall portion of the vessel and the determined first position of the posterior wall portion, and identifying the pulse wave traveling past a second vessel axial position using the determined second position of the anterior wall portion of the vessel and the determined second position of the posterior wall portion, and determining a period of elapsed time between the pulse wave passing the first vessel axial position and the pulse wave passing the second vessel axial position.

In any of the aspects or embodiments described above and herein, the step of determining said pulse wave velocity value using the first sensed signals and the second sensed signals may include identifying a pulse wave traveling past a first vessel axial position using the first sensed signals, and identifying the pulse wave traveling past a second vessel axial position using the second sensed signals, and determining a period of elapsed time between the pulse wave passing the first vessel axial position and the pulse wave passing the second vessel axial position.

According to another aspect of the present disclosure, a method of determining a physiologic parameter of a subject having at least one central artery and at least one peripheral artery is provided. The method includes: a) providing a first sensor and a second sensor, the first sensor and the second sensor each having an array of ultrasound transducers that includes at least a first ultrasound transducer and a second ultrasound transducer, the first ultrasound transducer and the second ultrasound transducer disposed along a linear axis and separated from one another by a distance, and a controller in communication with the first ultrasound transducer and the second ultrasound transducer; b) disposing the first sensor on a skin surface of a subject so that the linear axis of the first ultrasound transducer and the second ultrasound transducer of the first sensor substantially aligns with an axial length of a central artery; c) disposing the second sensor on a skin surface of a subject so that the linear axis of the first ultrasound transducer and the second ultrasound transducer of the second sensor substantially aligns with an axial length of a peripheral artery; d) determining a first central artery diameter at a first central artery axial position and a second central artery diameter at a second central artery axial position based on signals produced by the first sensor interrogating the central artery; e) determining a first peripheral artery diameter at a first peripheral artery axial position and a second peripheral artery diameter at a second peripheral artery axial position based on signals produced by the second sensor interrogating the peripheral artery; f) determining a central pulse wave velocity value in the central artery using the determined first central artery diameter and the second central artery diameter; g) determining a peripheral pulse wave velocity value in the peripheral artery using the determined first peripheral artery diameter and the second peripheral artery diameter; and h) determining a physiologic parameter of a subject based on the determined central pulse wave velocity value and the determined peripheral pulse wave velocity.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DESCRIPTION

The present disclosure is directed to a system and method for continuously and non-invasively sensing blood vessels for the purpose of determining and/or monitoring physiologic parameters such as blood vessel diameter ("AD") and pulse wave velocity ("PWV"), and which can use such parameters to infer other physiologic parameters and states such as, but not limited to, arterial blood pressure and arterial tone, and to determine and/or monitor the effects of vasoactive agents. To facilitate the description, the present disclosure is described hereinafter as applied to arteries. The present disclosure is not limited to producing information from arteries, however, and may be used to produce information regarding veins and blood flows there through.

Figure 1:
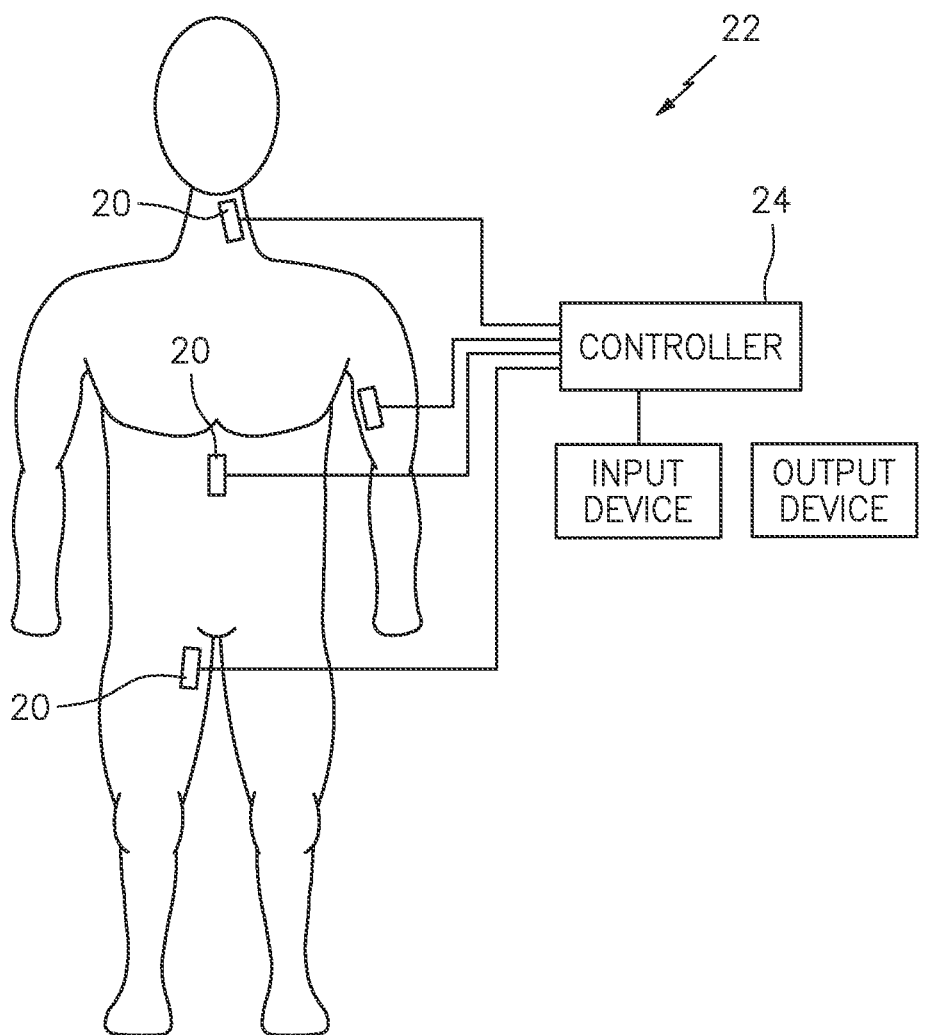
FIG. 1 is a diagram of the present disclosure system, illustrating sensors attached to a subject in a plurality of different positions.

Aspects of the present disclosure include one or more sensors 20 operable to communicate with a controller, and a system 22 that includes the aforesaid one or more sensors 20 and controller 24. FIG. 1 diagrammatic illustrates a present disclosure system 22 embodiment with a plurality of sensors 20 disposed on the subject in alignment with various arteries, the sensors 20 in communication with the controller 24.

Figure 2:
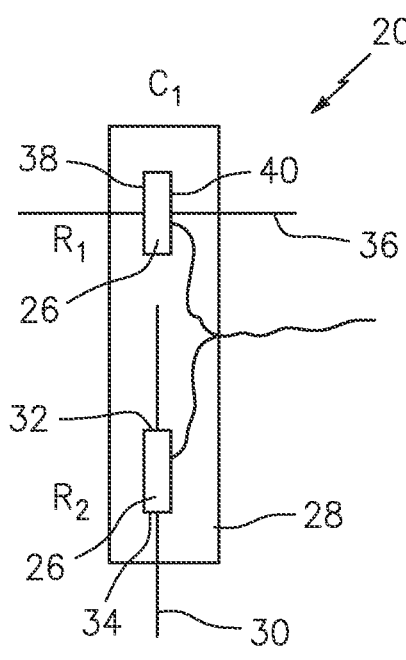
FIG. 2 is a diagrammatic top view of a sensor having a transducer array with a single column and two rows.
Figure 3:
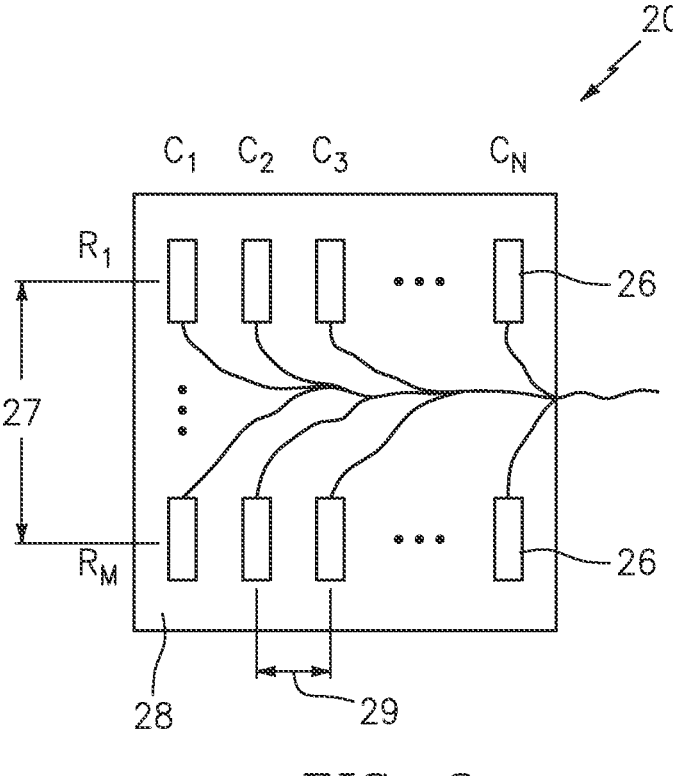
FIG. 3 is a diagrammatic top view of a sensor having a transducer array with a plurality of columns and a plurality of rows.

The sensor(s) 20 includes an array of ultrasonic transducers 26 attached to a base panel 28. The array of ultrasonic transducers 26 includes transducers arranged to in at least one column and at least two rows. As an example, the array shown in FIG. 2 is a one column (C1) array having two rows (R1, R2). As another example, the array shown in FIG. 3 includes a plurality of columns and a plurality of rows; e.g., "N" number of columns (C1, C2, C3 . . . CN), with each column having "M" number of rows (R1 . . . RM), where "N" and "M" are integers. The ultrasonic transducers 26 within a column are separated from one another by an intercolumn distance 27, and the ultrasonic transducers 26 within a row are separated from one another by an interrow distance 29. The intercolumn distances 27 may be uniform within an array or may be non-uniform. The interrow distances 29 may be uniform within an array or may be non-uniform.

The ultrasonic transducers 26 may be configured for two-way signal communication with the controller 24 via hard wire or by wireless means. Each ultrasonic transducer 26 is configured to both transmit and receive ultrasonic signals. In some embodiments, an ultrasonic transducer 26 may include one or more elements that both transmit and receive ultrasonic signals. In alternative embodiments, an ultrasonic transducer 26 may include one or more elements dedicated to transmitting ultrasonic signals and one or more elements dedicated to receiving ultrasonic signals. The term "ultrasonic signals" as used herein refers to the mechanical pressure waves produced and/or received by the transducer, which pressure waves are sometimes referred to as pressure waves, sound waves, sound pulses, acoustic waves, or the like. The transducers 26 are configurable to produce the ultrasonic signals at one or more predetermined frequencies and wavelengths; e.g., typically within the range of 1-10 MHz.

Figure 4:
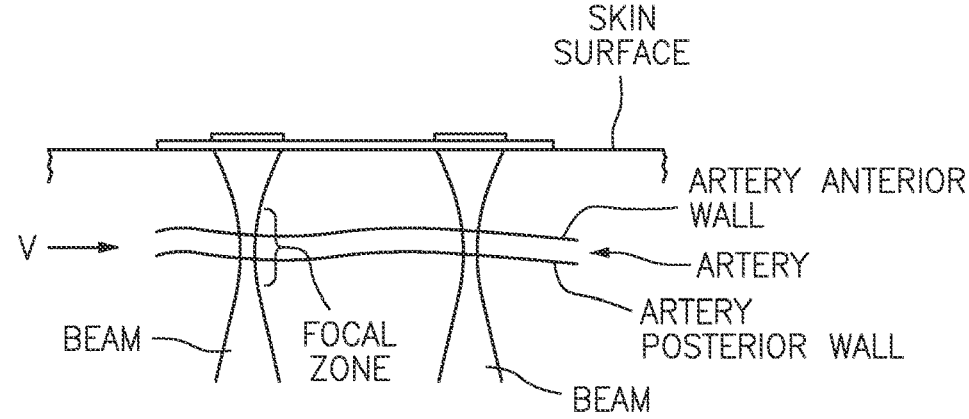
FIG. 4 is a diagrammatic side view of a sensor disposed on the skin of a subject with a plurality of transducers interrogating a vessel within the subject's tissue.
Figure 5A:
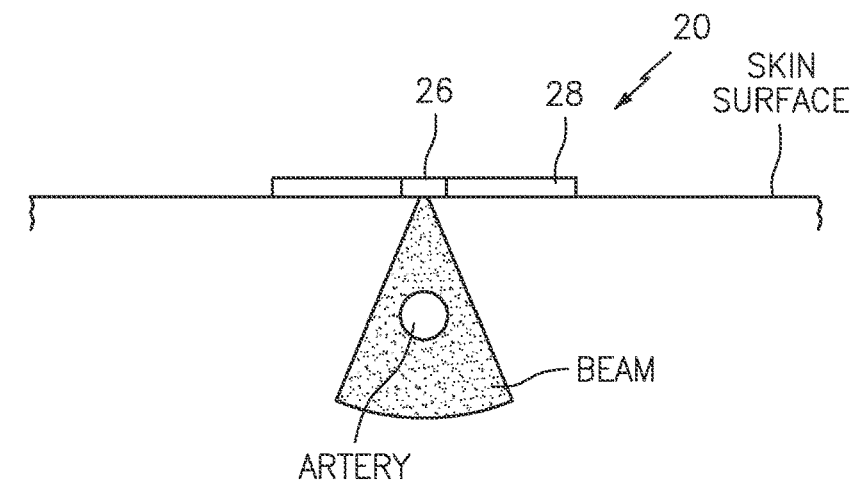
FIG. 5A is a diagrammatic end view of a sensor disposed on the skin of a subject with a single transducer interrogating a vessel within the subject's tissue in a transverse plane.
Figure 5B:
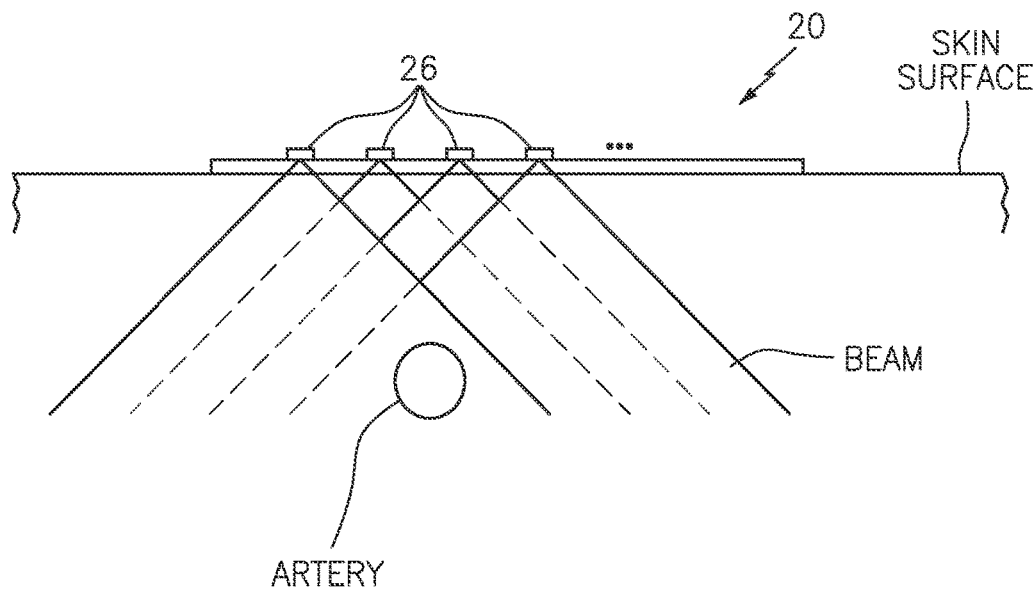
FIG. 5B is a diagrammatic end view of a sensor disposed on the skin of a subject with a plurality of transducers interrogating a vessel within the subject's tissue in a transverse plane.

The ultrasonic transducers 26 may be configured to produce a focused beam that includes a focal zone located at the anticipated depth of the artery, and that extends laterally a distance at least equal to and preferably greater than the anticipated width of the artery. In some embodiments, a single ultrasonic transducer 26 within in each array row may be configured to produce a beam (e.g., a focused beam) having a focal zone located at the anticipated depth of the artery (e.g., See FIG. 4), and that extends laterally a distance at least equal to and preferably greater than the anticipated width of the artery (e.g., See FIG. 5A). In some embodiments, a plurality of transducers 26 within a row of the array (e.g., see FIG. 3) may be collectively configured or controlled using beam forming techniques to produce a beam that depthwise includes a focal zone at the anticipated depth of the artery, and that extends laterally a distance at least equal to and preferably greater than the anticipated width of the artery (e.g., See FIG. 5B).

Figure 6A:
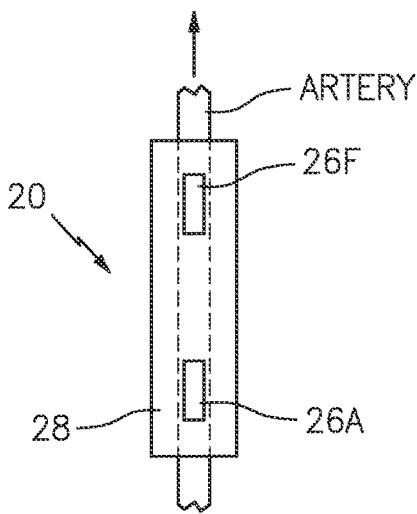
FIG. 6A is a diagrammatic top view of a sensor having a transducer array with a single column and two rows, substantially aligned with a vessel.
Figure 6B:
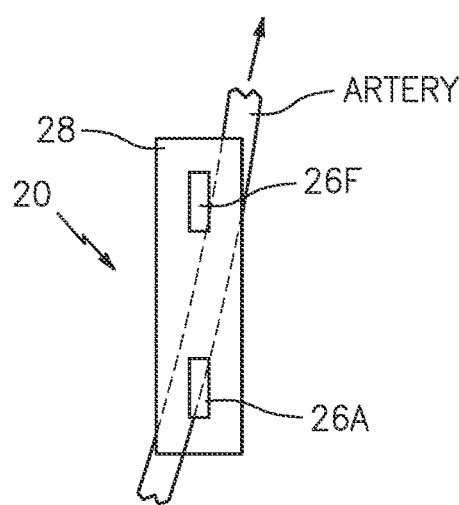
FIG. 6B is a diagrammatic top view of a sensor having a transducer array with a single column and two rows, axially misaligned with a vessel.
Figure 6C:
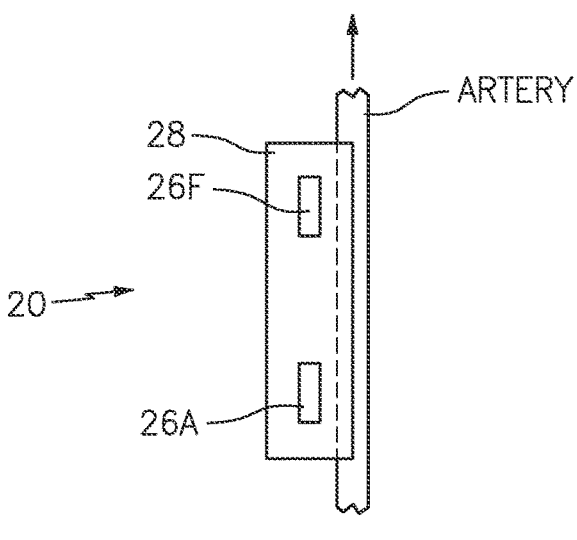
FIG. 6C is a diagrammatic top view of a sensor having a transducer array with a single column and two rows, laterally misaligned with a vessel.

An example of an acceptable transducer 26 is one that has a length and a width, and the length is greater than the width. The specific dimensions of length and the width may be described in terms of the wavelength of the ultrasonic signal produced by the transducer 26. The length of the transducer 26 is greater than the wavelength of the ultrasonic signal produced by the transducer 26. The width of the transducer 26 is on the order of the wavelength, preferably less than or equal to the wavelength, of the ultrasonic signal produced by the transducer 26. The length of each ultrasonic transducer 26 may be described as extending along a lengthwise axis 30 (see FIG. 2) between a first lengthwise end 32 and a second lengthwise end 34. The width of each ultrasonic transducer 26 may be described as extending along a widthwise axis 36 between a first lateral side 38 and a second lateral side 40. The width of the beam extends laterally a distance at least equal to and preferably greater than the anticipated width of the artery (a predetermined value may be used to approximate the artery width), and consequently accommodates misalignment of the beam with the artery initially, or misalignment that occurs as a result of movement by the subject. To diagrammatically illustrate, FIGS. 6A-6C illustrates a forward transducer 26F and an aft transducer 26A disposed within a column of the transducer 26 array. The forward transducer 26F is located downstream of the aft transducer 26A, such that blood traveling within the artery will pass the aft transducer 26A before it passes the forward transducer 26F. FIG. 6A illustrates an artery substantially aligned with both the forward and aft transducers 26F, 26A. FIG. 6B illustrates an artery axially misaligned with the array column having the forward and aft transducers 26F, 26A. FIG. 6C illustrates an artery laterally misaligned with array column having the forward and aft transducers 26F, 26A. In FIGS. 6B and 6C, the width of the beam (substantially transverse to the artery) accommodates the misalignment between the column axis and the artery. The present disclosure in not limited to the above described transducer 26 configuration. Non-limiting examples of acceptable ultrasonic transducer types include transducers having piezoelectric elements; e.g., PZT (lead zirconate titanate) based transducers, CMUT (capacitive micromachine) transducers, PMUT (piezoelectric micromachine) transducers, and like devices operable to transform mechanical energy into electrical energy and vice versa. As indicated above, the ultrasonic transducers 26 are configured to both transmit and receive ultrasonic signals, and may include one or more elements that both transmit and receive ultrasonic signals, or one or more elements dedicated to transmitting ultrasonic signals and one or more elements dedicated to receiving ultrasonic signals. An ultrasonic transducer 26 that is configured as a linear array of elements is particularly useful with the present disclosure.

The base panel 28 may be configured to be sufficiently deformable (e.g., flexible and/or stretchable) to permit the sensor 20 to conform to the subject's skin surface. An example of a base panel 28 material is one comprising a silicone elastomeric material. The present disclosure is not, however, limited to any particular base panel 28 material. The base panel 28 is configured so that the ultrasonic transducers 26 are held in contact with the subject's skin surface when the sensor 20 is attached to the subject. The base panel 28 (and therefore the sensor 20) may be attached to a skin surface (e.g., an arm surface, leg surface, torso surface, or the like) by various means; e.g., by a mechanical fastener, or an adhesive layer, etc.). The present disclosure is not limited to any particular means of attaching a sensor 20 to a subject.

The controller 24 is in signal communication with the sensor(s) 20 to perform the functions described herein. The controller 24 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system to accomplish the same algorithmically and/or coordination of system components. The controller 24 may include a single memory device or a plurality of memory devices. The present disclosure is not limited to any particular type of non-transitory memory device, and may include read-only memory, random access memory, volatile memory, non-volatile memory, static memory, dynamic memory, flash memory, cache memory, and/or any device that stores digital information. The controller 24 may include, or may be in communication with, an input device that enables a user to enter data and/or instructions, and may include, or be in communication with, an output device configured, for example to display information (e.g., a visual display or a printer), or to transfer data, etc. Communications between the controller 24 and other system components may be via a hardwire connection or via a wireless connection.

During operation of at least some present disclosure systems, at least one sensor 20 is attached to the subject and positioned in alignment with a blood vessel of the subject. Non-limiting examples of blood vessels that may be sensed include the descending aortic artery, a carotid artery, a femoral artery, and a brachial artery. The sensor 20 is attached to the subject and positioned so that a first transducer 26 (e.g., an aft transducer 26A) within an array column is substantially aligned with the artery at a first axial position and a second transducer 26 (e.g., a forward transducer 26F) in the same array column is substantially aligned with the artery vessel at a second axial position. In terms of the transducer example described above, the transducers 26 may be disposed within the column such that the lengthwise axis of each transducer 26 is substantially parallel to the columnar direction (and therefore substantially parallel to the flow within vessel), and the widthwise axis 36 is perpendicular to the columnar direction (and therefore substantially perpendicular to the flow within the vessel).

The ultrasound transducers 26 are operated to produce an incident beam of ultrasonic signal configured to permit the posterior and anterior walls of the artery to be identified and located relative to one another. The transducers 26 are typically operated to produce the aforesaid ultrasonic signals a plurality of times during a cardiac cycle. The ultrasonic signals that form the beam reflect off of elements within the tissue, including the anterior and posterior walls of the artery being investigated. The reflected ultrasonic signals reflect back towards and are sensed by the transducers 26. The transducers 26, in turn, produce electronic signals that are communicated to the controller 24. The features within the reflected signals that correspond to the anterior and posterior walls of the artery may be extracted from all of the reflected signals (and the electronic signals representative thereof) by the controller 24 using stored instructions for example based on heuristic methods, including but not limited to detection of maximum values, cross-correlation, and/or machine learning techniques. The reflected ultrasonic signals that correspond to the anterior and posterior walls of the artery permit an arterial diameter (AD) determination; e.g., the difference between the signal time-indexes that correspond to the (time/space) location of the posterior and anterior walls may be subtracted to obtain the diameter of the artery at a given location. The reflected ultrasonic signals that correspond to the anterior and posterior walls of the artery also permit a pulse wave velocity (PWV) determination; e.g., a time period that is proportional to the pulse wave velocity (PWV) may be determined using a cross-correlation between the diameter signals per cardiac cycle from forward and aft transducers 26F, 26A within a column of the transducer array (or from collective forward transducers and collective aft transducers in multiple columns).

Figures 7A, 7B, 7C, 7D, 7E, 7F:
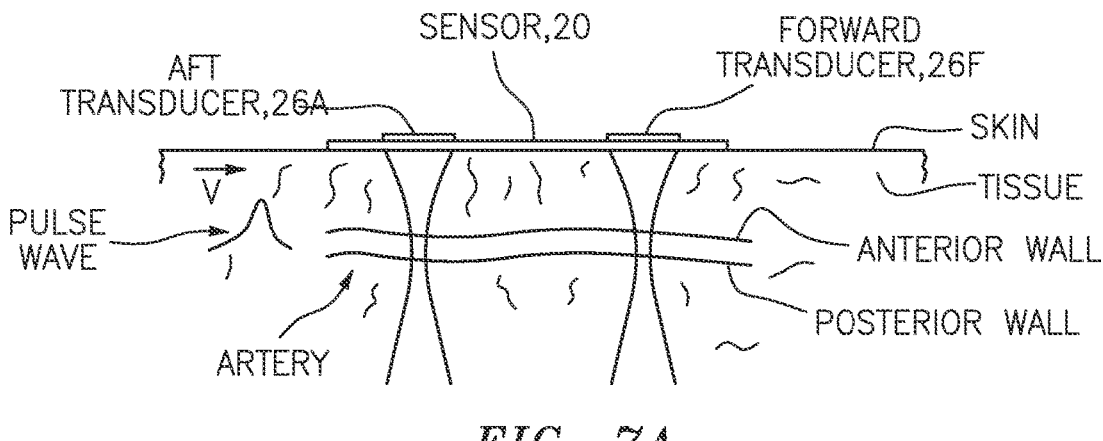
FIG. 7A is a diagrammatic side view of a sensor disposed on the skin of a subject with a plurality of transducers interrogating a vessel within the subject's tissue.
FIG. 7B is a graph of firing sequence (Y-axis) versus arrival time (X-axis) for a plurality of ultrasonic signal firings from a first transducer during a period of time.
FIG. 7C illustrates a graph of arrival time (Y-axis) versus time (X-axis) collectively for the plurality of ultrasonic signal firings from the first transducer shown in FIG. 7B.
FIG. 7D is a graph of firing sequence (Y-axis) versus arrival time (X-axis) for a plurality of ultrasonic signal firings from a second transducer during a period of time.
FIG. 7E illustrates a graph of arrival time (Y-axis) versus time (X-axis) collectively for the plurality of ultrasonic signal firings from the second transducer shown in FIG. 7D.
FIG. 7F illustrates a graph of diameter changes (Y-axis) versus the period of time, with a first curve representative of the data from first transducer and a second curve representative of the data from the second transducer.

FIGS. 7A-7F diagrammatically illustrate the operation described above. In FIG. 7A, a sensor 20 is shown disposed on a skin surface of a subject, and forward and aft transducers 26F, 26A disposed in an array column that is aligned with an artery. The forward and aft transducers 26F, 26A are diagrammatically shown producing ultrasonic beams focused depthwise on the artery. FIG. 7B illustrates a graph of firing sequence (Y-axis) versus arrival time (X-axis) for a plurality of ultrasonic signal firings from the aft transducer 26A during a period of time (e.g., a number of firings that occur during a cardiac cycle). The signals depicted in the graph of FIG. 7B diagrammatically illustrate features associated with both the anterior and posterior walls of the artery being investigated. FIG. 7C illustrates a graph of arrival time (Y-axis) versus time (X-axis) collectively for the plurality of ultrasonic signal firings from the aft transducer 26A shown in FIG. 7B. In similar fashion, FIG. 7D illustrates a graph of firing sequence (Y-axis) versus arrival time (X-axis) for a plurality of ultrasonic signal firings from the forward transducer 26F during the period of time, and FIG. 7E illustrates a graph of arrival time (Y-axis) versus time (X-axis) collectively for the plurality of ultrasonic signal firings from the forward transducer 26F. FIG. 7F illustrates a graph of diameter changes (Y-axis) versus the period of time, with a first curve 42 representative of the data from aft transducer 26A and a second curve 44 representative of the data from the forward transducer 26F. The difference between the first and second curves 42, 44 can be used to determine a pulse wave velocity value within the artery. The diagrammatic graphic illustration of the ultrasonic signal interrogation, and diameter change and pulse wave velocity determination shown in FIGS. 7A-7F is provided to facilitate explanation of an embodiment of the present disclosure. The present disclosure is not limited to a graphic determination; e.g., the algorithmic instructions stored within the controller 24 can perform the aforesaid algorithmic instructions to produce numeric values and/or visual displays for the system operator. In some embodiments, the algorithmic instructions stored within the controller 24 may include one or more empirical databases that are used to provide information relating a physiologic state to the determined arterial diameter and pulse wave velocity values; e.g., one or more empirical data bases that relate the determined values to a determination or inference of arterial blood pressure values, arterial tone values, stenosis, etc.

Utilizing both arterial diameter and pulse wave velocity measurements, the present disclosure is able to provide information regarding physiologic parameters and states with a higher degree of sensitivity and specificity than is possible using most conventional measuring devices and methodologies. For example, a variety of factors can cause variations in a subject's arterial blood pressure variations; e.g., cardiac output, vessel compliance, blood volume, blood viscosity, etc. A conventional blood pressure cuff provides no direct information on vasoconstriction—only blood pressure. Similarly, conventional arterial tone techniques estimate local arterial tone values by measuring the arrival of a pulse wave relative to an electrocardiogram signal (i.e., "ECG" or EKG"), which local arterial tone values may not accurately reflect central arterial tone values. The present disclosure, in contrast, enables an accurate determination of arterial diameter and pulse wave velocity values (in central or peripheral arteries), which values can subsequently be used to determine or infer additional physiologic parameters (e.g., arterial blood pressure, arterial tone, etc.) on a continuous basis with a higher degree of sensitivity and specificity than is possible using most conventional measuring devices and methodologies. Indeed, the ability of the present disclosure to provide arterial diameter and pulse wave velocity values in both central and peripheral arteries, can provide a clinician significant information relating to differences between central and peripheral vascular tone and/or states. As yet another example, conventional diagnoses of stenosis may be based on arterial diameter measurements and Doppler signals. These conventional techniques are typically not performed continuously and can involve at least some degree of discomfort. The present disclosure, in contrast, enables an accurate determination of arterial diameter and pulse wave velocity values (in central or peripheral arteries) on a continuous basis, which values can subsequently be used to non-invasively diagnose stenosis.

In addition, the present disclosure is able to provide information regarding the response of a subject to vasoactive agents based on the determined arterial diameter and pulse wave velocity measurements. To determine the effect of a vasoactive agent on a subject using conventional techniques, a clinician may use a blood pressure cuff to determine whether or not the subject has reacted to a vasoactive agent. As stated above, however, a variety of factors can influence a subject's arterial blood pressure. Consequently, using conventional techniques, a determination of the effect of a vasoactive agent is at best indirect and inferential, and may be subject to errors attributable to other factors. In addition, determinations of the effect of a vasoactive agent made using conventional techniques are likely based on periodically collected information; e.g., conventional arterial blood pressure data collected periodically using a blood pressure cuff. The present disclosure, in contrast, enables the determination of arterial diameter and pulse wave velocity values (in central or peripheral arteries) continuously with a high degree of accuracy, and therefore provides significant information regarding a subject's response to a vasoactive agent with greater specificity and sensitivity that is possible using conventional techniques. The ability of the present disclosure to provide such information on a continuous basis also provides more immediate oversight, including the provision of trend data on a real time basis.

Embodiments of the present disclosure may also be used to provide correlative information based on the combination of arterial diameter and pulse wave velocity measurements. For example, an increase in arterial diameter and a decrease in pulse wave velocity is indicative of a decrease in vasoconstriction, and a decrease in arterial diameter and an increase in pulse wave velocity is indicative of an increase in vasoconstriction. These correlations (both positive and negative) of non-invasively produced arterial diameter and pulse wave velocity values available using the present disclosure can provide useful information indicative of physiologic states.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein. For example, in the exemplary embodiments described above within the Detailed Description portion of the present specification, elements are described as individual units and shown as independent of one another to facilitate the description. In alternative embodiments, such elements may be configured as combined elements.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A system for non-invasively sensing a blood vessel, the system comprising:
   a sensor having an array of ultrasound transducers that includes at least a first ultrasound transducer and a second ultrasound transducer, the array having a first column, a first row, and a second row, the first row spaced apart from the second row by an intercolumn distance, the first ultrasound transducer disposed in the first column and the first row, and the second ultrasound transducer disposed in the first column and the second row;
   wherein the first ultrasound transducer is configured to produce first ultrasonic signals at a first wavelength, and the first ultrasound transducer has a first length that extends along a first lengthwise axis and the first length is greater than the first wavelength, and a first width that is equal to or less than the first wavelength; and
   wherein the second ultrasound transducer is configured to produce second ultrasonic signals at a second wavelength, and the second ultrasound transducer has a second length that extends along a second lengthwise axis and the second length is greater than the second wavelength and a second width that is equal to or less than the second wavelength; and
   wherein the first lengthwise axis of the first ultrasound transducer and the second lengthwise axis of the first ultrasound transducer are aligned with one another along a column axis of the first column; and
   a controller in communication with the first ultrasound transducer and the second ultrasound transducer, and a memory storing instructions, wherein the instructions when executed cause the controller to:
   control the first ultrasound transducer to produce a first beam of first ultrasonic signals and to receive reflected first ultrasonic signals, and to communicate first sensed signals to the controller that are representative of the reflected first ultrasonic signals;
   control the second ultrasound transducer to produce a second beam of second ultrasonic signals and to receive reflected second ultrasonic signals, and to communicate second sensed signals to the controller that are representative of the reflected second ultrasonic signals;
   determine a first vessel diameter value using the first sensed signals;
   determine a second vessel diameter value using the second sensed signals; and
   determine a pulse wave velocity value using the first sensed signals and the second sensed signals.

2. The system of claim 1, wherein the first beam of first ultrasonic signals is configured to have a first focal zone disposed at a predetermined depth, and a first width at the predetermined depth that is equal to or greater than a predetermined vessel diameter.

3. The system of claim 2, wherein the second beam of second ultrasonic signals is configured to have a second focal zone disposed at the predetermined depth, and a second width at the predetermined depth that is equal to or greater than the predetermined vessel diameter.

4. The system of claim 1, wherein the instructions when executed cause the controller to determine a first position of an anterior wall portion of the blood vessel using the first sensed signals, and determine a first position of a posterior wall portion of the blood vessel using the first sensed signals, and determine the first vessel diameter value using the determined first position of the anterior wall portion of the vessel and the determined first position of the posterior wall portion.

5. The system of claim 4, wherein the instructions when executed cause the controller to determine a second position of the anterior wall portion of the blood vessel using the second sensed signals, and determine a second position of the posterior wall portion of the blood vessel using the second sensed signals, and determine the second vessel diameter value using the determined second position of the anterior wall portion of the vessel and the determined second position of the posterior wall portion.

6. The system of claim 5, wherein the instructions when executed cause the controller to identify a pulse wave traveling past a first vessel axial position using the determined first position of the anterior wall portion of the blood vessel and the determined first position of the posterior wall portion, and to identify the pulse wave traveling past a second vessel axial position using the determined second position of the anterior wall portion of the blood vessel and the determined second position of the posterior wall portion, and to determine a period of elapsed time between the pulse wave passing the first vessel axial position and the pulse wave passing the second vessel axial position.

7. The system of claim 6, wherein the first vessel axial position and the second vessel axial position are separated by the intercolumn distance.

8. The system of claim 1, wherein the instructions when executed cause the controller to identify a pulse wave traveling past a first vessel axial position using the first sensed signals and to identify the pulse wave traveling past a second vessel axial position using the second sensed signals, and to determine a period of elapsed time between the pulse wave passing the first vessel axial position and the pulse wave passing the second vessel axial position.

9. The system of claim 8, wherein the first vessel axial position and the second vessel axial position are separated by the intercolumn distance.

10. The system of claim 1, wherein the first column is orthogonal to the first row and to the second row.

11. A method of non-invasively sensing a blood vessel, comprising:

providing a sensor having an array of ultrasound transducers that includes at least a first ultrasound transducer and a second ultrasound transducer, the array having a first column, a first row, and a second row, the first row spaced apart from the second row by an intercolumn distance, the first ultrasound transducer disposed in the first column and the first row, and the second ultrasound transducer disposed in the first column and the second row, and a controller in communication with the first ultrasound transducer and the second ultrasound transducer;

wherein the first ultrasound transducer is configured to produce first ultrasonic signals at a first wavelength, and the first ultrasound transducer has a first length that extends along a first lengthwise axis and the first length is greater than the first wavelength, and a first width that is equal to or less than the first wavelength; and wherein the second ultrasound transducer is configured to produce second ultrasonic signals at a second wavelength, and the second ultrasound transducer has a second length that extends along a second lengthwise axis and the second length is greater than the second wavelength and a second width that is equal to or less than the second wavelength; and wherein the first lengthwise axis of the first ultrasound transducer and the second lengthwise axis of the second ultrasound transducer are aligned with one another along a column axis of the first column; and disposing the sensor on a skin surface of a subject so that the column axis of the first column substantially aligns with an axial length of the blood vessel;

operating the first ultrasound transducer to interrogate the blood vessel with a first beam of first ultrasonic signals, and to receive reflected first ultrasonic signals, the first ultrasound transducer configured to produce first sensed signals representative of the reflected first ultrasonic signals;

operating the second ultrasound transducer to interrogate the blood vessel with a second beam of second ultrasonic signals, and to receive reflected second ultrasonic signals, the second ultrasound transducer configured to produce second sensed signals representative of the reflected second ultrasonic signals;

determining a first vessel diameter value using the first sensed signals;

determining a second vessel diameter value using the second sensed signals; and determining a pulse wave velocity value using the first sensed signals and the second sensed signals.

12. The method of claim 11, wherein the blood vessel is an artery.

13. The method of claim 11, wherein the first beam of first ultrasonic signals is configured to have a first focal zone disposed at a predetermined depth, and a first width at the predetermined depth that is equal to or greater than a predetermined vessel diameter.

14. The method of claim 13, wherein the second beam of second ultrasonic signals is configured to have a second focal zone disposed at the predetermined depth, and a second width at the predetermined depth that is equal to or greater than the predetermined vessel diameter.

15. The method of claim 11, wherein the step of determining said first vessel diameter value using the first sensed signals includes determining a first position of an anterior wall portion of the blood vessel using the first sensed signals, and determining a first position of a posterior wall portion of the blood vessel using the first sensed signals, and determining the first vessel diameter value using the determined first position of the anterior wall portion of the vessel and the determined first position of the posterior wall portion.

16. The method of claim 15, wherein the step of determining said second vessel diameter value using the second sensed signals includes determining a second position of the anterior wall portion of the blood vessel using the second sensed signals, and determining a second position of the posterior wall portion of the blood vessel using the second sensed signals, and determining the second vessel diameter value using the determined second position of the anterior wall portion of the vessel and the determined second position of the posterior wall portion.

17. The method of claim 16, wherein the step of determining said pulse wave velocity value using the first sensed signals and the second sensed signals includes identifying a pulse wave traveling past a first vessel axial position using the determined first position of the anterior wall portion of the vessel and the determined first position of the posterior wall portion, and identifying the pulse wave traveling past a second vessel axial position using the determined second position of the anterior wall portion of the vessel and the determined second position of the posterior wall portion, and determining a period of elapsed time between the pulse wave passing the first vessel axial position and the pulse wave passing the second vessel axial position.

18. The method of claim 11, wherein the step of determining said pulse wave velocity value using the first sensed signals and the second sensed signals includes identifying a pulse wave traveling past a first vessel axial position using the first sensed signals, and identifying the pulse wave traveling past a second vessel axial position using the second sensed signals, and determining a period of elapsed time between the pulse wave passing the first vessel axial position and the pulse wave passing the second vessel axial position.

19. The system of claim 1, wherein the first wavelength equals the second wavelength.

20. The system of claim 1, wherein the array of ultrasound transducers includes a plurality of first ultrasound transducers disposed in the first row, wherein adjacent first ultrasound transducers in the first row are separated from one another by an interrow distance, and the array includes a plurality of second ultrasound transducers in the second row, wherein adjacent second ultrasound transducers in the second row are separated from one another by the interrow distance.

21. The system of claim 1, wherein the array of ultrasound transducers includes a third ultrasound transducer disposed in the first row separated from the first ultrasound transducer in the first row by an interrow distance, and a fourth ultrasound transducer in the second row disposed in the second row separated from the second ultrasound transducer in the second row by the interrow distance; and wherein the third ultrasound transducer and the fourth ultrasound transducer are disposed in a second column;

wherein the third ultrasound transducer is configured to produce third ultrasonic signals at a third wavelength, and the third ultrasound transducer has a third length that extends along a third lengthwise axis and the third length is greater than the third wavelength, and a third width that is equal to or less than the third wavelength; and wherein the fourth ultrasound transducer is configured to produce fourth ultrasonic signals at a fourth wavelength, and the fourth ultrasound transducer has a fourth length that extends along a fourth lengthwise axis and the fourth length is greater than the fourth wavelength and a fourth width that is equal to or less than the fourth wavelength; and wherein the third lengthwise axis of the third ultrasound transducer and the fourth lengthwise axis of the fourth ultrasound transducer are aligned with one another along a column axis of the second column; and wherein the column axis of the first column and the column axis of the second column are parallel one another.

* * * * *